United States Patent [19]
Tanaka et al.

[11] Patent Number: 4,732,479
[45] Date of Patent: Mar. 22, 1988

[54] PARTICLE ANALYZING APPARATUS

[75] Inventors: Masayuki Tanaka, Kawasaki; Shinichi Ohe, Yokohama; Naoki Yuguchi, Yokohama; Akira Tago, Yokohama, all of Japan

[73] Assignee: Canon Kabushiki Kaisha, Tokyo, Japan

[21] Appl. No.: 918,981

[22] Filed: Oct. 15, 1986

[30] Foreign Application Priority Data

Oct. 18, 1985 [JP] Japan ................. 60-232804
Oct. 28, 1985 [JP] Japan ................. 60-241006
Nov. 11, 1985 [JP] Japan ................. 60-252334

[51] Int. Cl.$^4$ .................. G01N 15/02; G01N 21/00
[52] U.S. Cl. .................................. 356/336; 356/339; 356/343; 356/400
[58] Field of Search ............... 356/336, 338, 339, 343, 356/400

[56] References Cited
U.S. PATENT DOCUMENTS

| | | | |
|---|---|---|---|
| 3,627,424 | 12/1971 | Dorman et al. | 356/338 |
| 4,053,229 | 10/1977 | McClaney | 356/343 |
| 4,299,489 | 11/1981 | Thery et al. | 356/336 |
| 4,387,993 | 6/1983 | Adrian | 356/336 |
| 4,411,525 | 10/1983 | Ogawa | 356/339 |
| 4,558,947 | 12/1985 | Wardlaw | 356/336 |
| 4,643,566 | 2/1987 | Ohe et al. | 356/72 |
| 4,665,553 | 5/1987 | Gershman et al. | 356/338 |
| 4,679,939 | 7/1987 | Curry et al. | 356/339 |
| 4,690,561 | 9/1987 | Ito | 356/339 |

*Primary Examiner*—Bruce C. Anderson
*Attorney, Agent, or Firm*—Fitzpatrick, Cella, Harper & Scinto

[57] ABSTRACT

A particle analyzing apparatus is provided with an irradiating optical system for applying a light beam to a particle to be examined flowing through a circulation portion in a flow cell, a photometering optical system for photometering the light from the particle to be examined irradiated by the irradiating optical system, and moving means for rendering a base bed on which the flow cell and the photometering optical system are placed movable relative to the irradiating optical system.

17 Claims, 19 Drawing Figures

FIG. 10B

FIG. 15A
FIG. 15B
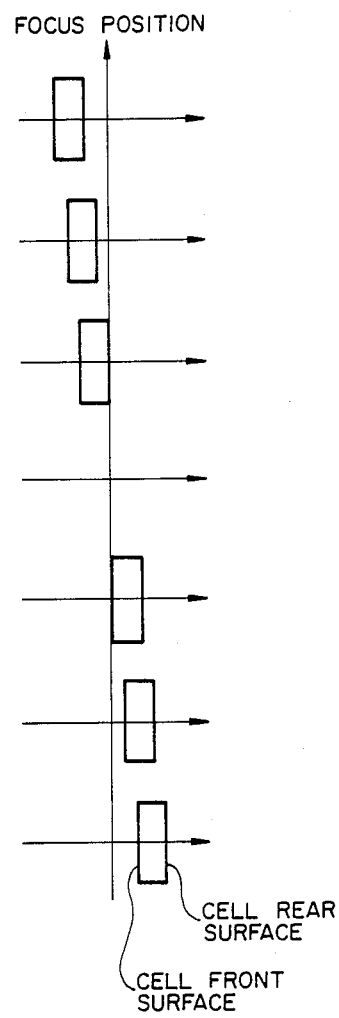
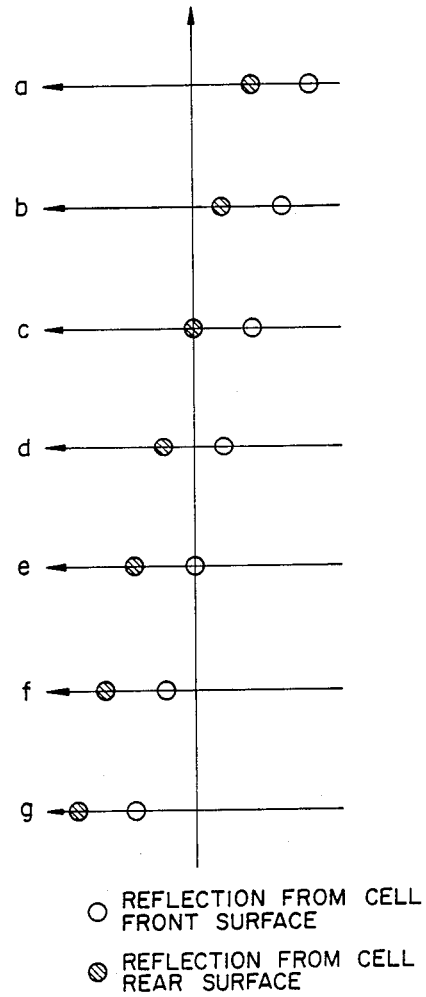
○ REFLECTION FROM CELL FRONT SURFACE
⊘ REFLECTION FROM CELL REAR SURFACE

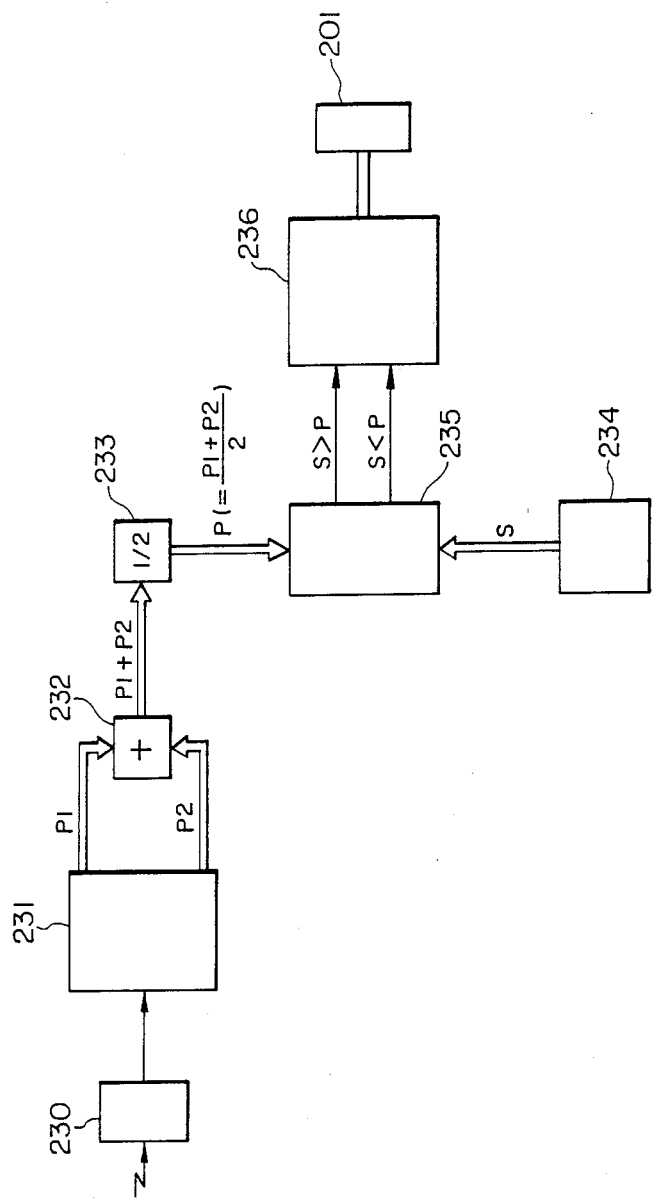

PARTICLE ANALYZING APPARATUS

BACKGROUND OF THE INVENTION

1. Field of the Invention

This invention relates to a particle analyzing apparatus in a flow sightmeter or the like in which simple adjustment of the positions of a photometering optical system and a flow cell relative to an irradiating optical system is possible.

2. Related Background Art

In a conventional particle analyzing apparatus used in a flow sightmeter or the like, as shown in FIG. 1 of the accompanying drawings, a parallel laser beam L from a laser light source, not shown, is applied to a particle S to be examined flowing at a high speed through the central circulation (or flowing) portion 2 of a flow cell 1 having a minute cross-section of 200 μm×200 μm, for instance, while being wrapped in sheath liquid, through the intermediary of a condensing lens 3, as shown in FIG. 2 of the accompanying drawings. Forward scattered light scattered by the particle S to be examined is condensed on a photoelectric detector 5 through an objective 4, whereby information chiefly about the size of the particle S to be examined is obtained. Also, the sidewise scattered light and fluorescence scattered light from the particle S to be examined are condensed on a photoelectric detector 7 through an objective 6, whereby important information chiefly about the complexity of the interior of the particle S to be examined can be obtained.

To accomplish accurate measurement in a flow sightmeter, the optical axis of the laser beam L must be coincident with the center of the flow cell 1 and the scattered lights from the particle S to be examined must be accurately condensed by the photometering objectives 4 and 6. For this purpose, the axis of the flow of the particle S to be examined and the condensing lenses 4 and 6 must be accurately adjusted relative to the optical axis of the laser beam L, but in the conventional apparatus, the flow cell 1 and the photometering optical system are separate from each other and, when the axis of the flow of the particle S to be examined is adjusted relative to the optical axis of the laser beam L in a state in which the flow cell 1 has been finely moved, the position of the optical system for sidewise scattered light deviates and therefore, it is also necessary to adjust the optical system for sidewise scattered light and thus, operation becomes cumbersome and moreover, it is difficult to effect sufficiently accurate adjustment.

SUMMARY OF THE INVENTION

It is an object of the present invention to provide a particle analyzing apparatus in which a photometering optical system and a flow cell are fixed, whereby alignment can be easily carried out by mere adjustment of the axis of the flow of a particle to be examined relative to the optical axis of a laser beam and measurement of high accuracy is possible.

It is a further object of the present invention to provide a particle analyzing apparatus in which a light beam transmitted through the edge portion of a flow cell can be detected to thereby automatically accomplish alignment of the flow cell and the irradiating optical system.

It is still a further object of the present invention to provide a particle analyzing apparatus in which the positional relation between the reflected lights from the opposite wall surfaces of a flow cell can be detected to thereby automatically adjust or confirm the relative relation between the flow cell and the photometering optical system.

BRIEF DESCRIPTION OF THE DRAWINGS

FIGS. 13 to 16 show an embodiment in which the positional relation between the reflected lights from the opposite wall surfaces of a flow cell can be detected to thereby adjust or confirm the relative relation between the flow cell and the photometering optical system, FIGS. 13 and 14 showing the construction of an optical system, FIGS. 15A, 15B and 15C illustrating the relation between the center of the flow cell and the focus position, and FIG. 16 being a block circuit diagram of a signal processing part and a driving part.

DESCRIPTION OF THE PREFERRED EMBODIMENTS

A first embodiment of the present invention will hereinafter be described with reference to FIGS. 3 to 7.

Figure 1:
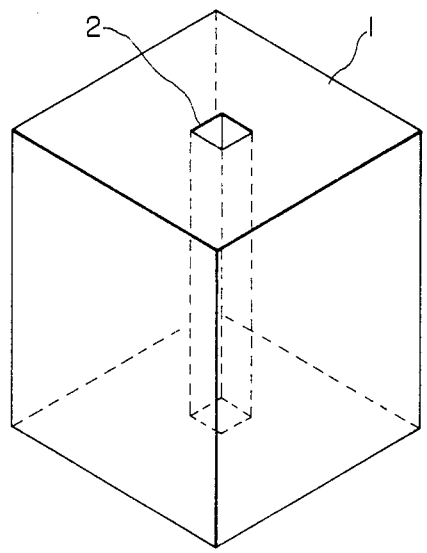
FIG. 1 is a perspective view of a flow cell.
Figure 2:
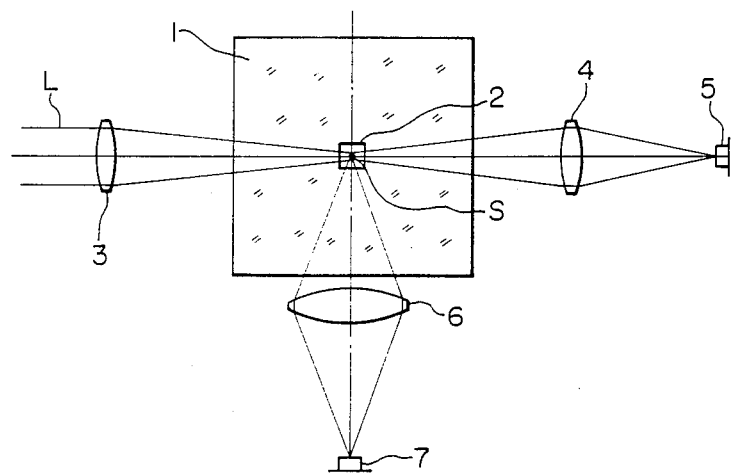
FIG. 2 shows the arrangement of an optical system according to the prior art.
Figure 3:
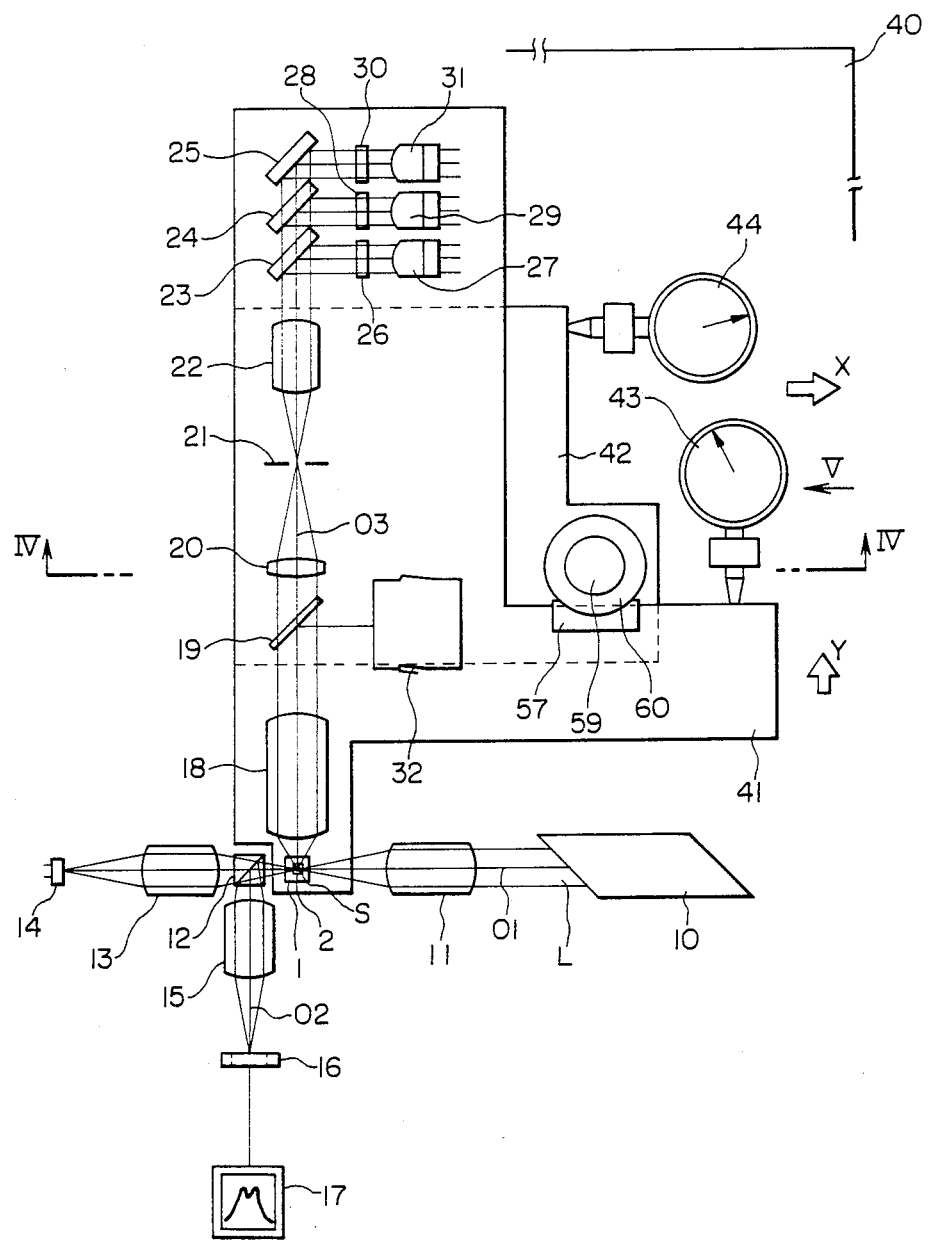
FIGS. 3 to 6 show an embodiment of a particle analyzing apparatus according to the present invention, FIG. 3 showing the construction of an optical system and an alignment apparatus, FIG. 4 being a cross-sectional view taken along line IV—IV of FIG. 3, FIG. 5 being a side view as seen from the direction of arrow V in FIG. 3, and FIG. 6 showing the distribution of intensity of light in the aligned state.

FIG. 3 is a plan view of an optical system and an alignment apparatus. A circulation portion 2 for passing sample liquid therethrough in a vertical direction perpendicular to the plane of the drawing sheet is provided at the center of a flow cell 1, a laser light source 10 is disposed in a direction orthogonal to the flow of the sample liquid, and an imaging lens 11 for adjusting the imaged shape of a laser beam L is disposed on an optical axis 01 to direct the light emitted from the laser light source 10 to the circulation portion 2. Also, on the forward scattered light side from a particle S to be examined by the laser beam L, a beam splitter 12, an objective 13 and a photoelectric detector 14 are disposed in succession from the flow cell 1 side. An objective 15 and an array-like photoelectric detector 16 are disposed on an optical axis opposite to the beam splitter 12 to detect the distributed state of the light beam divided by the beam splitter 12. The output of the photoelectric detector 16 is connected to a monitor 17 for observing the distribution of intensity of light. On an optical axis 03 orthogonal to the axis of flow of the particle S to be examined and to the optical axis 01, a photometering objective 18, a half-mirror 19, a condensing lens 20, a stop 21, a condensing lens 22, dichroic mirrors 23, 24 and a mirror 25 are disposed in succession from the flow cell 1 side. A barrier filter 26 and a photoelectric detector 27 are disposed in the direction of reflection of the dichroic mirror 23, a barrier filter 28 and a photoelectric detector 29 are disposed in the direction of reflection of the dichroic mirror 24, and a barrier filter 30 and a photoelectric detector 31 are disposed in the direction of reflection of the mirror 25. Photomultipliers for increasing a weak light and making it detectable are used in these photoelectric detectors 27, 29 and 31. On the reflection side of the half-mirror 19, there is provided an auto-focus unit 32 which is used to adjust or confirm the focuses of the flow cell 1 and an optical system for photometering the sidewise scattered light and fluorescence.

The laser light source 10 to the photoelectric detector 14 on the optical axis 01 and the objective 15 and photoelectric detector 16 on the optical axis 02 are fixed on a base plate 40 after adjustment of their axes. Also, the flow cell 1 and the objective 18 to the mirror 25 on the optical axis 03, the barrier filters 26, 28, 30, the photoelectric detectors 27, 29, 31 and the auto-focus unit 32 are disposed on a stage 41 movable in Y direction parallel to the optical axis 03 after adjustment of the focus, and a stage 42 movable in X direction parallel to the optical axis 01 is interposed between the base plate 40 and the stage 41. The amount of movement of the stage 41 in Y direction may be measured by a dial gauge 43, and the amount of movement of the stage 42 in X direction may be measured by a dial gauge 44.

Figure 4:
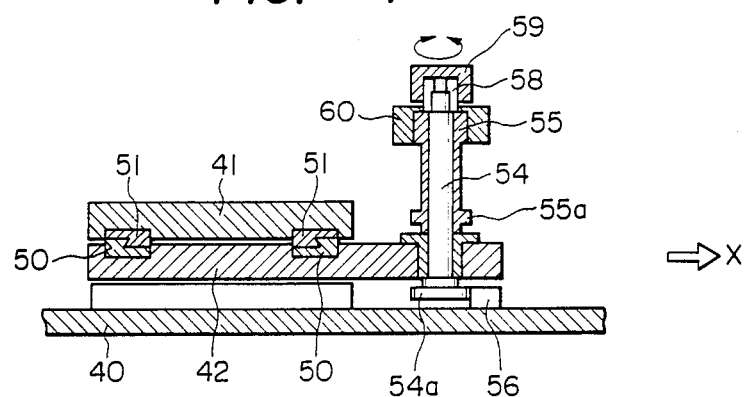
Figure 5:
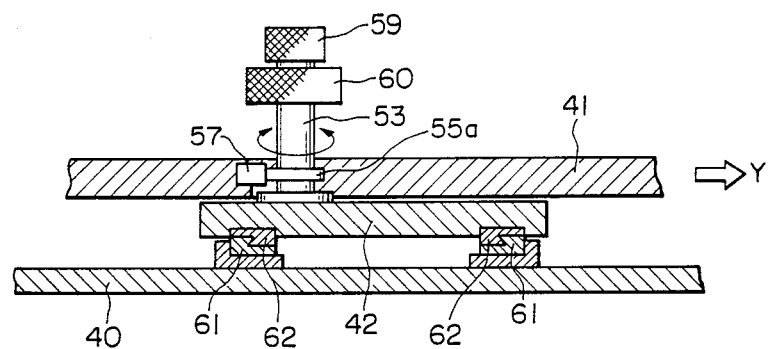

Referring to FIG. 4 which is a cross-sectional view taken along line IV—IV of FIG. 3, two rails 50 are laid on the upper surface of the stage 42 in Y direction, and by the rails 50 being fitted to rails 51 on the lower surface of the stage 41, the stage 41 is parallel-movable in Y direction relative to the stage 42. A bearing 53 is provided at the right end of the stage 42, and a cam shaft 54 is rotatably supported on the bearing 53. Further, a cam shaft 55 is fitted to the outer side of the cam shaft 54 and is rotatable relative to the cam shaft 54. Eccentric cams 54a and 55a are provided around the cam shafts 54 and 55, respectively, and the stages 41 and 42 are biased by springs, not shown, so that these cams 54a and 55a are normally in contact with a guide 56 fixed to the base plate 40 and a guide 57 fixed to the stage 41 as shown in FIG. 5, respectively. Further, an anti-slippage member 58 and a rotatable knob 59 for rotating the cam shaft 54 are mounted on the upper portion of the cam shaft 54, and a rotatable knob 60 is mounted on the upper portion of the cam shaft 55.

Referring now to FIG. 5 which is a side view taken in the direction of arrow V of FIG. 3, two rails 61 are laid on the base plate 40 in X direction and are fitted to two rails 62 on the lower surface of the stage 42 so that the stage 42 is parallel-movable in X direction relative to the base plate 40.

The laser beam L emitted from the laser light source 10 enters the circulation portion 2 of the flow cell 1 through the imaging lens 11, and part of the forward scattered light by the particle S to be examined travels rectilinearly through the beam splitter 12 and is condensed on the photoelectric detector 14 through the objective 13, whereby the intensity of light thereof is metered. The remainder of said forward scattered light is reflected by the beam splitter 12 and condensed on the array-like photoelectric detector 16 through the objective 15, whereby the positional relation of the particle S to be examined to the optical axis 01 is detected.

Also, the sidewise scattered light by the particle S to be examined enters the dichroic mirrors 23, 24 and the mirror 25 through the photometering objective 18, the half-mirror 19, the condensing lens 20, the stop 21 and the condensing lens 22, and the reflected lights of respective wavelength ranges by these mirrors 23, 24 and 25 are condensed on the photoelectric detectors 27, 29 and 31, respectively, through the barrier filters 26, 28 and 30, whereby the intensity of light is metered.

To adjust the flow cell 1 and the photometering optical system with respect to X direction and Y direction, the rotatable knob 59 of the cam shaft 54 may first be rotated, whereupon the cam 54a may rotate and slide on the guide 56 and therefore, the stage 42 can parallel-move in X direction relative to the base plate 40 by an amount corresponding to the amount of lift of the cam 54a. Likewise, the rotatable knob 60 fixed to the cam shaft 55 may be rotated, whereupon the cam 55a may rotate and slide on the guide 57 and therefore, the stage 41 can parallel-move in Y direction relative to the stage 42 by an amount corresponding to the amount of lift of the cam 55a.

The amounts of parallel movement in X and Y directions can be in a considerably slight range because the amount of lift relative to the angle of rotation can be set arbitrarily by the cams 54a and 55a, and these amounts of movement can be read by the dial gauges 43 and 44 fixed on the base plate 40.

The procedure of adjusting the present particle analyzing apparatus will now be described. The sidewise photometering optical system is axis-adjusted relative to the optical axis 03, whereafter it is fixed to the stage 41 and alignment of the flow cell 1 relative to the photometering optical system is effected. For this purpose, by the use of the auto-focus unit 32, the flow cell 1 is parallel-moved independently in X and Y directions and, in a position wherein the focus is adjusted to the center of the flow cell 1, the flow cell 1 is fixed to the stage 41. Accordingly, the flow cell 1 and the sidewise photometering optical system can be parallel-moved together with each other on the stage 41 in X and Y directions relative to the base plate 40.

Figure 6:

To effect alignment of the flow of the particle S to be examined with the optical axis 01 while moving the adjusted flow cell 1 on the optical axis 01 by moving the stages 41 and 42, use is made, for example, of quasi-sample liquid absorbing a light of the wavelength range of the laser beam L, instead of the particle S to be examined. Part of the laser beam L emitted from the laser light source 10 is absorbed by the quasi-sample liquid, and the distribution of intensity of light during the absorption is measured by the array-like photoelectric detector 16, the output signal of which is observed by the monitor 17. When the optical axis 01 and the center of the flow of the quasi-sample liquid are coincident with each other, the distribution of intensity of light observed is a bilaterally symmetrical wave form in which the central portion of a Gaussian distributed wave form is concave as shown in FIG. 6. However, when the optical axis 01 and the center of the flow of the quasi-sample liquid are not coincident with each other, the central concave portion will deviate to the left or the right and the distribution will not exhibit a symmetrical wave form. In such case, adjustment may be effected by turning the rotatable knob 60 to parallel-move the flow cell 1 in Y direction until the wave form on the monitor exhibits bilateral symmetry.

Also, to confirm the coincidence between the focus position of the laser beam L from the laser light source 10 and the center of the flow of the quasi-sample liquid, the rotatable knob 59 may be turned to parallel-move the flow cell 1 in X direction, thereby effecting adjustment so that the concave valley portion of the Gaussian distribution on the monitor becomes lowest in level and narrowest in width. By the use of such an adjusting method, alignment of the flow of the quasi-sample liquid with the optical axis 01 can be accomplished.

In the present embodiment, the optical system for photometering the sidewise scattered light of the applied light on the optical axis 03 by the particle S to be examined and the fluorescence is placed on the stages 41 and 42 to which the flow cell 1 is fixed, and these stages 41 and 42 are parallel-moved in Y direction or X direction to thereby accomplish the alignment of the laser beam L with the optical axis 01, but a similar effect may be obtained by moving the base plate 40 on which the laser light source 10 and the optical system for photometering the forward scattered light are placed relative to the optical system for photometering the sidewise scattered light and the fluorescence to thereby effect alignment. In the present embodiment, a method using the cam shafts 54 and 55 is used for fine adjustment of the stages 41 and 42, but of course, other driving mechanisms may also be used to effect adjustment of the optical axis.

Detailed description will now be made of an embodiment in which a light beam transmitted through the edge portion of the flow cell is detected, whereby alignment of the flow cell with the irradiating optical system is accomplished.

Figure 7:
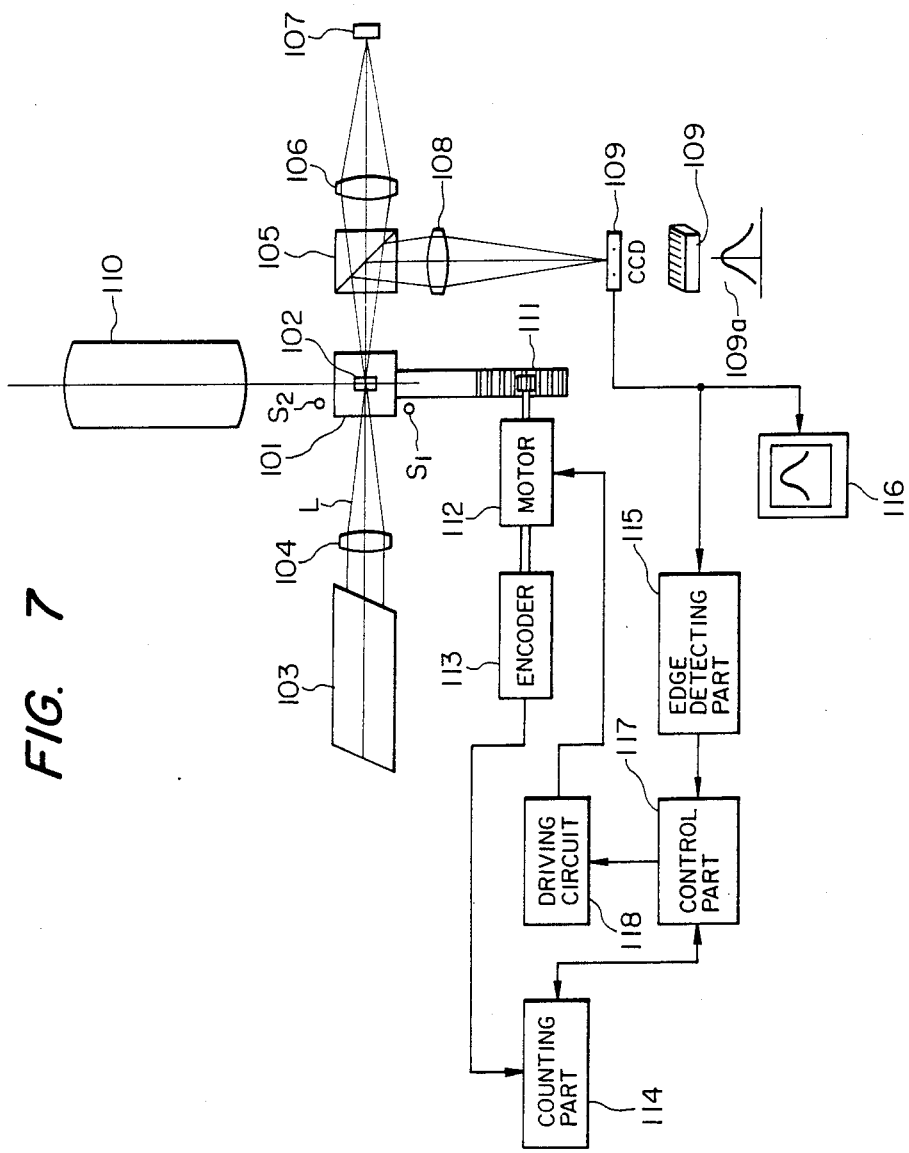
FIGS. 7 to 12 show an embodiment in which a light beam transmitted through the edge portion of a flow cell is detected to thereby accomplish alignment of the flow cell and the irradiating optical system, FIG. 7 showing the construction of an optical system and a signal processing part, FIGS. 8, 9 and 11 showing the relative positional relation between the irradiation optic axis and the flow cell and the output wave form of the distribution of intensity of light corresponding to the positional relation from a light array sensor, FIGS. 10A and B showing the processed wave form of the output signal from the light array sensor obtained in the edge detecting part, and FIG. 12 showing the construction of another embodiment.

FIG. 7 shows the construction of the optical system and the signal processing system. A circulation portion 102 through which sample liquid pass in a direction perpendicular to the plane of the drawing sheet is provided at the center of a flow cell 101. A laser light source 103 is disposed sidewise of the flow cell 101, and an imaging lens 104 is interposed between the flow cell 101 and the laser light source 103, and on the side of the extension of the optical axis thereof which is opposite to the flow cell 101, there are disposed in succession a beam splitter 105, a convex lens 106 and a photoelectric detector 107. A convex lens 108 and a one-dimensional light array sensor 109 comprising, for example, CCD (charge coupled device) are provided on the reflection side of the beam splitter 105. Further, a sidewise photometering system 110 is disposed sidewise of the flow cell 101 orthogonal to the laser beam L and the direction of circulation of sample liquid. A connecting part 111 having a gear is attached to the flow cell 101 so that the flow cell 101 may be driven in a direction orthogonal to the irradiation optic axis by a motor 112 through the connecting part 111. Revolution of the motor 112 is detected by an encoder 113, the output pulse of which is put out to a counting part 114. The output of the light array sensor 109 is connected to an edge detecting part 115 and a monitor 116 and the output of the edge detecting part 115 is connected to a control part 117, the output of which may revolve the motor 112 through a driving circuit 118. Transmission and reception of a signal may be effected between the control part 117 and the counting part 114.

The forward scattered light from the particle to be examined by the laser beam L is condensed on the photoelectric detector 107 through the beam splitter 105 and the convex lens 106.

The cross-sectional distribution of intensity of the laser beam L from the laser light source 103 presents a Gaussian distribution, and the laser beam L is imaged on the circulation portion 102 of the flow cell 101 through the imaging lens 104. The distribution of intensity of the laser beam L at this imaging position is likewise a Gaussian distribution. When the sample liquid is flowing through the circulation portion 102 in the flow cell 1 for the purpose of measurement while being wrapped in sheath liquid, it is necessary that the center of the Gaussian distribution of intensity by the laser beam L be aligned with the center of the circulation portion 102. That is, to maintain good measurement accuracy, it is required for the center of the flow of the sample liquid to be coincident with the peak position of the imaged beam.

Figure 8:
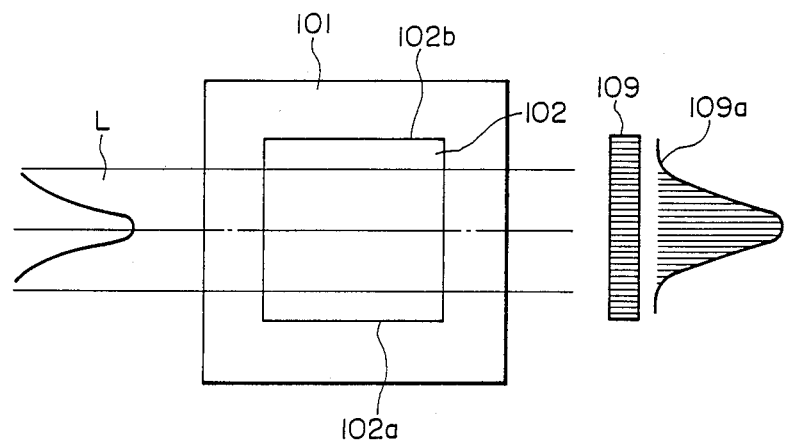

Part of the forward scattered light from the particle to be examined passed through the beam splitter 105 and the convex lens 108 is imaged on the one-dimensional light array sensor 109. If the center of the flow cell 101 is coincident with the optical axis in a plane perpendicular to the irradiation optical axis, the output wave form of the light array sensor 109 exhibits a perfect Gaussian distribution as shown at 109a, and if it is enlarged, it will be such as shown in FIG. 8.

Figure 9:
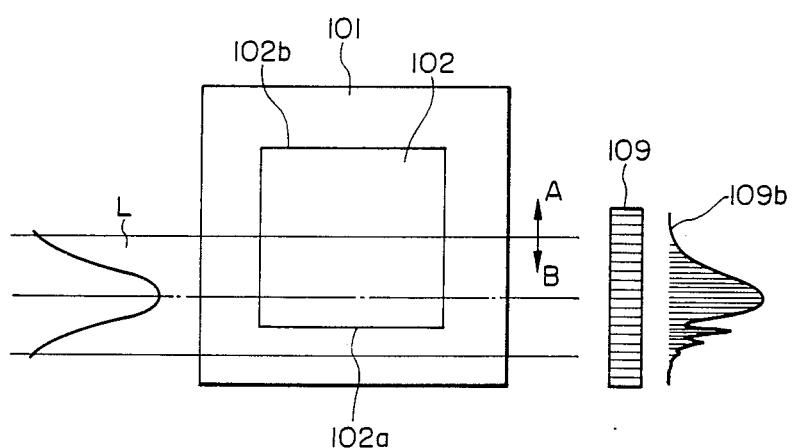

However, when there occurs a deviation in the plane perpendicular to the irradiation optical axis between the optical axis and the center of the flow cell 101 and as shown, for example, in FIG. 9, the laser beam L enters the edge portion 102a which is the inner wall of the circulation portion 102, the output wave form of the light array sensor 109 assumes a disturbed Gaussian distribution including a saw-tooth-like wave as shown at 109b. In the present embodiment, the disturbance of such Gaussian distribution is detected, whereby alignment of the center of the flow cell 101 with the irradiation optical axis is accomplished.

Figure 10A:
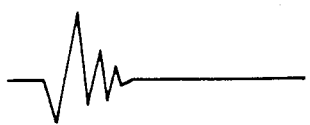

Assuming that the laser beam L enters the edge portion 102a of the circulation portion 102 as shown in FIG. 9, the output signal from the light array sensor 109 exhibits a disturbed Gaussian distribution as shown at 109b in FIG. 9, and this wave form is input to the edge detecting part 115. The edge detecting part 115 is a signal processing circuit comprised of a band-pass filter or the like, and it takes out only a saw-tooth-like wave as shown in FIG. 10A, generates a pulse as shown in FIG. 10B correspondingly to this wave form, and puts out binary signals "1" and "0" to the control part 117 when this pulse is generated. That is, when the laser beam L enters the edge portion 102a of the circulation portion 102, the signal "1" is put out from the edge detecting part 115 to the control part 117 having a circuit comprised of a microcomputer or the like, and when the laser beam L does not enter the edge portion 102a, the signal "0" is put out from the edge detecting part 115 to the control part 117.

When during adjustment, the flow cell 101 is moved in the direction of arrow A by the control signal from the control part 117 to the driving circuit 118, the laser beam L impinges on the edge portion 102a and the output wave form of the light array sensor 109 becomes such as indicated by a'. The control part 117 recognizes the signal "1" from the edge detecting part 115, stops the movement of the flow cell 1 through the driving circuit 118 and resets the content of the counting part 114 to 0. When the flow cell 101 is now moved in the direction of arrow B, the output pulses from the encoder 113 are input to the counting part 114 and each one pulse is added. When the flow cell 1 is thus moved in the direction of arrow B, the output of the edge detecting part 115 assumes the output condition of the normal Gaussian distribution shown at c' in FIG. 11 and the laser beam L now enters the edge portion 102b, and the edge detecting part 115 again puts out the signal "1", and the control part 117 recognizes this signal "1" and puts out a stop signal to the driving circuit 118.

Figure 11:
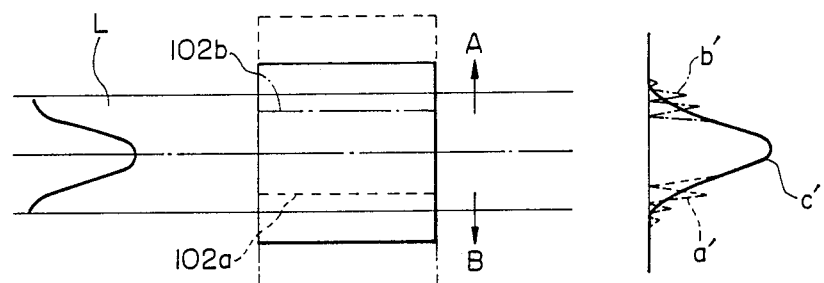

In this case, the pulse number N obtained in the counting part 114 corresponds to the amount of movement of the flow cell 101 in FIG. 11. Here, the counting part 114 is again reset, and the control part 117 puts out to the driving circuit 118 an instruction for moving the flow cell 101 in the direction of arrow A, and at a point of time whereat the pulse number counted by the counting part 114 has become N/2, the control part puts out a stop instruction to the driving circuit 118. The then position of the flow cell 101 is the medium distance of the initial amount of movement, i.e., the position in which the irradiation optical axis and the center of the flow cell 101 are coincident with each other. In this case, the output wave form obtained by the light array sensor 109 exhibits a normal Gaussian distribution free of disturbance as shown at c' in FIG. 11.

In the present embodiment, the range of movement of the flow cell 101 is mechanically limited and, if switches S1 and S2 are mounted at the opposite ends of the range of movement as shown in FIG. 7 so that the arrival of the flow cell 101 can be detected, the flow cell 101 will not deviate entirely from the laser beam L and excess movement of the flow cell 101 can be easily prevented. Also, by the output wave form of the light array sensor 109 being displayed on the monitor 116, the alignment condition can be observed. Further, in the present embodiment, the flow cell 101 and the sidewise photometering system 110 are made integral with each other so that the sidewise photometering system 110 is moved with the flow cell.

Figure 12:
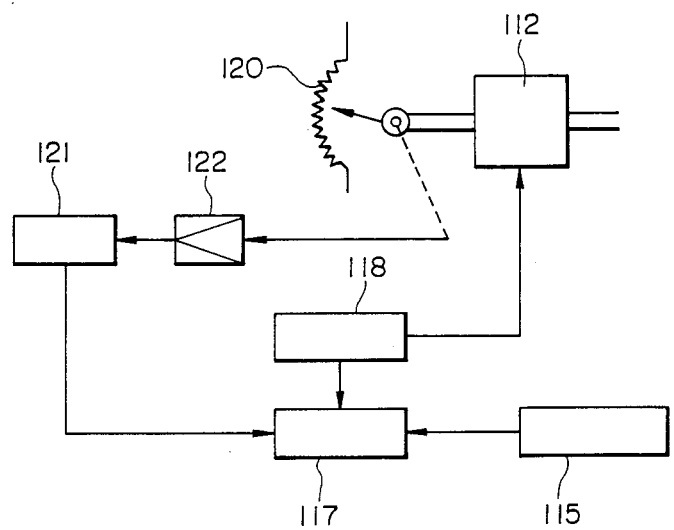

Also, as shown in FIG. 12, the encoder 113 of FIG. 7 may be replaced by a potentiometer 120 and the counting part 114 may be replaced by an A/D converter 121 so that the output of the potentiometer 120 may be read, whereby the position of the flow cell 101 can be recognized. Again in this case, as in the illustrated embodiment, the center of the flow cell 101 can be positioned at the midpoint and automatic alignment is possible. Reference numeral 122 designates an amplifier for amplifying the output of the potentiometer 121 and inputting it to the A/D converter 121.

FIGS. 13 to 16 show a embodiment in which the relative relation between the flow cell and the photometering optical system can be adjusted or confirmed by detecting the positional relation between the reflected lights from the opposite wall surfaces of the flow cell.

Figure 13:
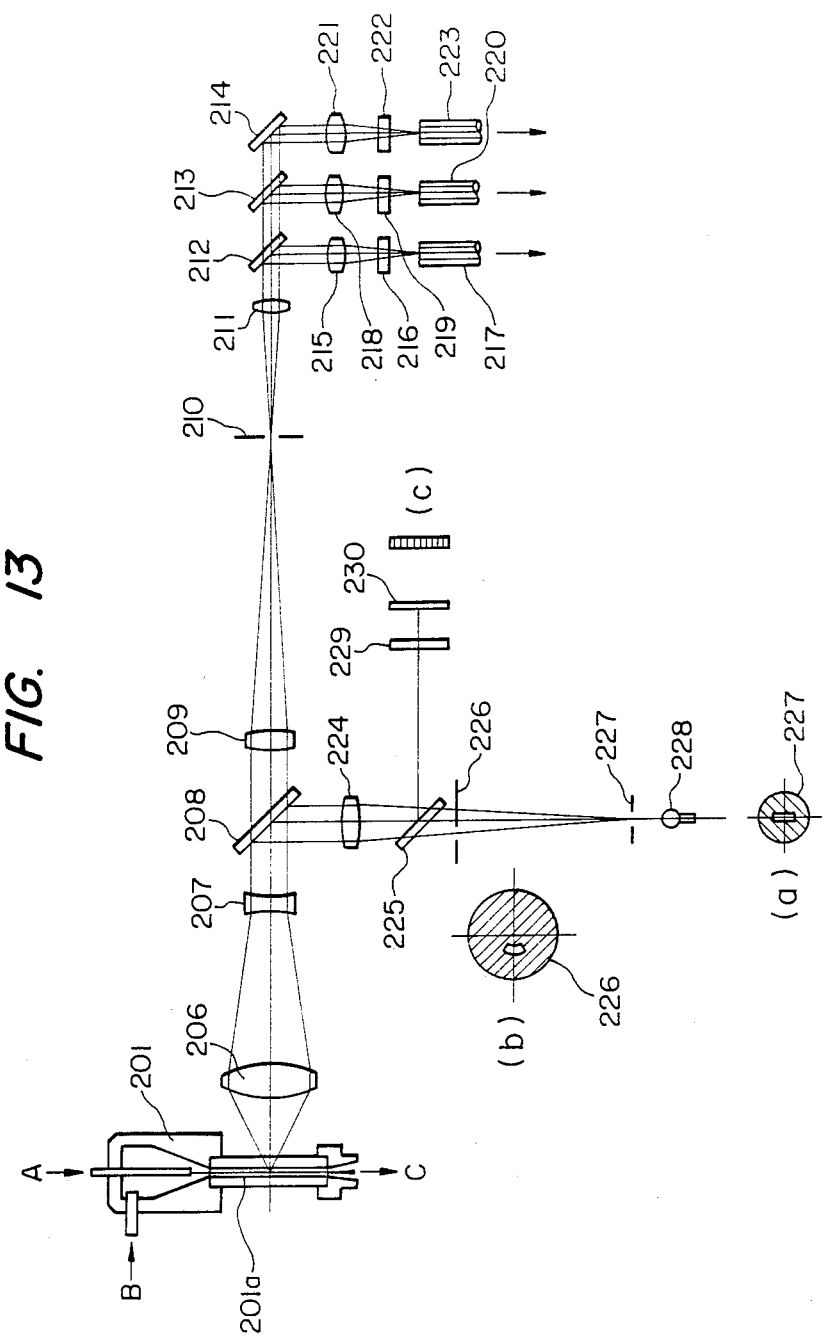
Figure 14:
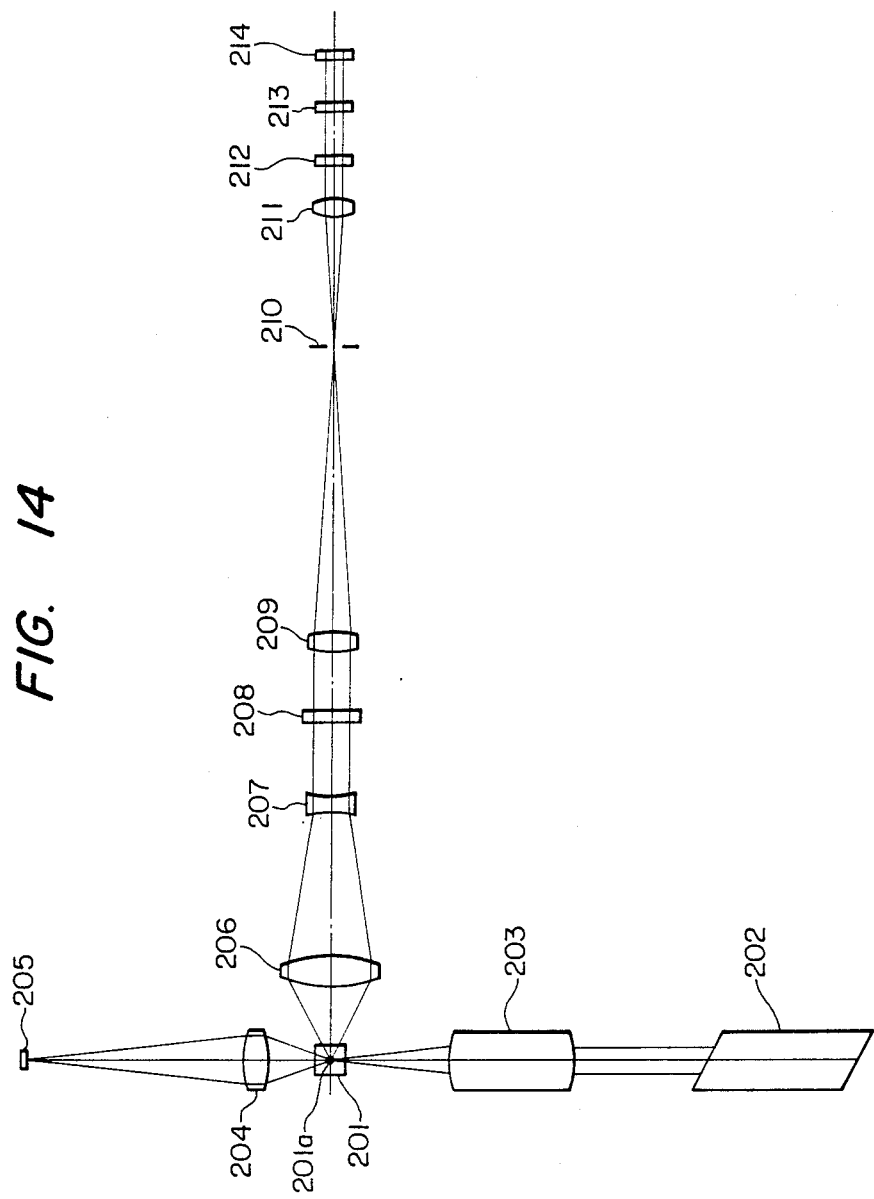

FIGS. 13 and 14 show the construction of a photometering optical system and an illuminating system. FIG. 13 is a view as seen from a direction parallel to the flow of sample liquid flowing through the flow cell 201, and FIG. 14 is a view as seen from a cross-sectional direction of the flow of sample liquid. A sample to be examined is poured into the flow cell 201 from the direction of arrow A and at the same time, sheath liquid is flows into the flow cell 201 from the direction of arrow B. In the circulation portion 201a of the flow cell 201, the sheath liquid is flowing in the state of a layer flow while wrapping the flow of sample liquid therein, and hydrodynamic focusing is effected, and the sheath liquid is discharged as a drain in the direction of arrow C. A laser beam emitted from an Ar+ laser light source 202 is imaged near the circulation portion 201a of the flow cell 201 through an imaging lens system 203. An objective 204 for condensing the forward scattered light by the particle to be examined and a photodetector 205 are disposed in the direction of rectilinear travel of the laser beam. On an optical axis perpendicular to the direction of incidence of the laser beam, there are disposed in succession a convex lens 206, a concave lens 207, an infrared light reflecting and visible light transmitting dichroic mirror 208, an imaging lens 209, a stop 210, a convex lens 211, dichroic mirrors 212, 213 and a reflecting mirror 214.

The dichroic mirror 212 has a characteristic of transmitting therethrough a light of longer wavelength than the wavelength 488 nm of the Ar+ laser light, and an imaging lens 215, a barrier filter 216 transmitting the wavelength of 488 nm therethrough and an optical guide 217 are disposed on the reflection side of the dichroic mirror 212. The dichroic mirror 213 has a characteristic of reflecting green light and transmitting red light therethrough, and an imaging lens 218, a bandpass filter 219 and an optical guide 220 are provided on the reflection side of the dichroic mirror 213. An imaging lens 221, a barrier filter 222 passing red light therethrough and an optical guide 223 are disposed on the reflection side of the reflecting mirror 214.

A focus detecting part comprising a projecting optical system and a measuring optical system is provided on the reflection side of the dichroic mirror 208, and on the optical axis, there are disposed, as the projecting optical system, a convex lens 224, a half-mirror 225, aperture masks 226, 227 and an infrared light source 228. Further, on the reflection side of the half-mirror 225, there are provided, as the photometering optical system, a barrier filter 229 and a light array sensor 230.

The forward scattered light of the laser beam by the particle to be examined is detected by the objective 204 and the photodetector 205. The reflected light from the particle to be examined which is dyed so as to emit fluorescence usually presents green or red fluorescence by the Ar+ laser light of wavelength 488 nm being applied thereto. It is known that PI used to detect the amount of DNA (deoxyribonucleic acid) emits red fluorescence and FITC used for the detection of cellular film surface antigen emits green fluorescence. Besides, the complicated structure of the interior of the particle to be examined is reflected in the sidewise scattered light by the application of the Ar+ laser light.

In order to obtain the information from such sidewise scattered light, the sidewise scattered light from the flow cell 201 passes through the objective system comprising the convex lens 206 and the concave lens 207 and through the imaging lens 209 and is once imaged at the focus position of the stop 210. The sidewise scattered light further passes through the convex lens 211 to the dichroic mirror 212, while light of shorter wavelength than the wavelength 488 nm of the Ar+ laser light is reflected by this dichroic mirror 212 and only the light of wavelength 488 nm passes through the imaging lens 215 and is imaged on the end surface of the optical guide 217 by the barrier filter 216, and is transmitted to and measured by a photodetector, not shown.

Of the light beam passed through the dichroic mirror 212, green light is reflected by the dichroic mirror 213 and passes through the imaging lens 218 and the barrier filter 219 passing only green light therethrough and enters the optical guide 220. Further, the light beam passed through the dichroic mirror 213 is reflected by the reflecting mirror 214 and passes through the imaging lens 221 and the barrier filter 222 passing only red light therethrough and enters the optical guide 223.

In the focus detecting part, the infrared light source 228 is emitting a light of the infrared range, and the irradiating light transmitted through the aperture mask 227 shown in FIG. 13(a) arrives at the dichroic mirror 208 via the aperture mask 226 having the pattern shown in FIG. 13(b), the half-mirror 225 and the convex lens 224, and is reflected to the left by the dichroic mirror 208 and is projected onto the flow cell 201 through the concave lens 207 and the convex lens 206. The width of the pattern of the mask 227 is more or less smaller than the width of the circulation portion 201a of the flow cell 201, and the projected light is reflected by the front and rear surfaces of the flow cell 201. However, if the reflection efficiency is neglected, the width of the pattern may be greater than the width of the circulation portion 201a.

Figure 15C:
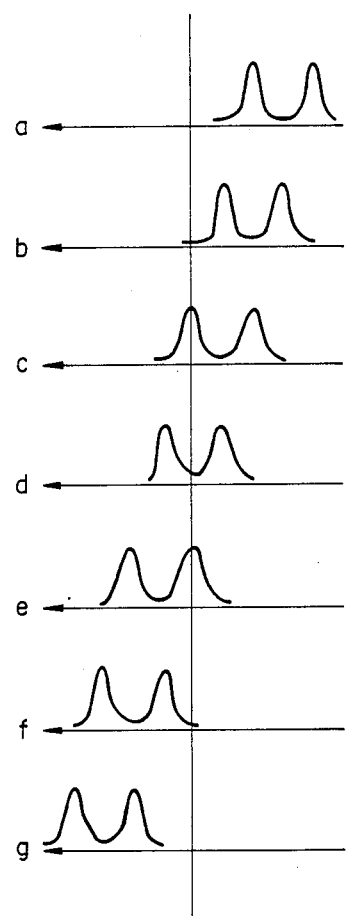

The pattern of the aperture mask 226 is such that the slit portion is eccentric from the optic axis, and this pattern is for causing the index mark by the mask 227 to enter the flow cell 201 from an oblique direction, but the projected light beam passes through this aperture mask 226 and therefore, if the flow cell 201 is in its normal position, i.e., a state in which the central portion thereof is optically conjugate with the photometering optical system, the state as shown at d in FIG. 15 will be obtained on the light array sensor 230 which is in a position optically equivalent to the convex lens 224. FIG. 15A shows the relation of the optically conjugate position of the entire flow cell 201, FIG. 15B shows the positions of the reflected lights from the front and rear surfaces of the flow cell 201, and FIG. 15C shows the photoelectrically converted output wave forms of the reflected lights from the front and rear surfaces of the flow cell 201. When the position of the focus thus deviates forwardly or rearwardly as indicated at a - c and e - g in FIG. 15A, the light beam is imaged at the positions shown in FIG. 15B and the signal wave forms shown in FIG. 15C are put out from the light array sensor 230.

The signal wave forms thus obtained in the focus detecting part are analyzed by a signal processing part and, when the focus position deviates, focus adjustment is effected automatically. The focus adjustment thus effected is adjusting the deviation of the focus relative to the direction of emergence of the sidewise scattered light in FIGS. 13 and 14 and moving the focus to the focus position of the optical system, but of course, a similar focus detecting part may also be disposed for the forward scattered light.

FIG. 16 is a block diagram of a circuit for automatic focus adjustment. The output signal from a light array sensor 230 is analyzed by a peak position detecting part 231. In this peak position detecting part 231, there are obtained a peak position P1 of the signal corresponding to the reflected light from the front surface of the flow cell 201 and a peak position P2 corresponding to the reflected light from the rear surface of the flow cell 201, and P1+P2 is calculated in an adder 232 and further, P=(P1+P2)/2 is found by a divider 233. This P is indicative of the current in-focus state of the projecting optical system, that is, the focus position of the objective optical system comprising the convex lens 206 and the concave lens 207. Accordingly, the output S of the optical focus position data preset in a reference position setting part 234 is compared with the output value P from the divider 233 by a comparator 235, and the output is sent to a cell driving part 236 so that P=S, whereby the position of the flow cell 201 is controlled. When P>S or P<S in the comparator 235, the driving direction for the cell driving part 236 is changed and the center of the flow cell 201 is controlled to the optical focus position and thus, automatic focusing is accomplished.

In the focus detecting part of the present embodiment, CCD is used as the light array sensor 230 and a signal wave form is extracted by causing the reflected light from the flow cell 201 by the projected light to scan electrically, but alternatively, a similar signal wave form may be obtained by attaching a mechanical driving mechanism to the photoelectric element and effecting the scanning. Also, if a microprocessor is introduced into the signal processing part so that each operation is carried out by a software, the circuit construction will become simple and a similar performance can be obtained. Of course, focus adjustment may also be accomplished by adjusting the objective system instead of moving the flow cell 201.

In the present embodiment, after the adjustment of the photometering optical system in the direction of the optic axis with respect to the flow cell or after the confirmation thereof, the flow cell and the photometering optical system are made integral and movable relative to the irradiating optical system as already described in connection with the previous embodiment.

We claim:

1. A particle analyzing apparatus comprising:
    an irradiating optical system having an axis for applying a light beam to a particle to be examined flowing through a circulation portion in a flow cell;
    a photometering optical system for photometering the light from the particle to be examined irradiated by said irradiating optical system; and
    moving means for rendering a base bed on which said flow cell and said photometering optical system are placed movable relative to said irradiating optical system.

2. A particle analyzing apparatus according to claim 1, wherein said photometering optical system photometers sidewise scattered light.

3. A particle analyzing apparatus according to claim 1, wherein said base bed is movable in the same plane containing the light beam irradiation optical axis in directions parallel to and perpendicular to the irradiation optical axis.

4. A particle analyzing apparatus according to claim 1, wherein a cam shaft is used as said moving means for said base bed and movement is accomplished by the utilization of the angle of rotation and the amount of lift of said cam shaft.

5. A particle analyzing apparatus according to claim 1, wherein a dial gauge is used as means for detecting the amount of movement of said base bed.

6. A particle analyzing apparatus comprising:
    an irradiating optical system for applying a light beam to a particle to be examined flowing through a circulation portion in a flow cell;

a photometering optical system for photometering the light from the particle to be examined irradiated by said irradiating optical system;

alignment detecting means for detecting the aligned state of said irradiating optical system in a direction orthogonal to an optical axis thereof with respect to said flow cell; and moving means for rendering a base bed on which said flow cell and said photometering optical system are placed movable relative to said irradiating optical system in a direction orthogonal to the optical axis of said irradiating optical system.

7. A particle analyzing apparatus according to claim 6, wherein said alignment detecting means is provided with an array-like photoelectric converter and a monitor provided conjugately with the circulation portion of said flow cell, and the distribution of intensity of light of the scattered light by said particle to be examined is observed by said monitor.

8. A particle analyzing apparatus according to claim 6, wherein said alignment detecting means is provided with edge detecting means for detecting the edge portion of said circulation portion by the light beam passed through said circulation portion, and control means for recognizing the edge detection signal from said edge detecting means and putting out a control signal so that the light beam may not enter said edge portion, and said moving means receives the instruction from said control means and moves said flow cell in a direction orthogonal to the irradiating optical axis.

9. A particle analyzing apparatus according to claim 8, wherein said edge detecting means detects said edge portion by the disturbance of a Gaussian distribution wave form obtained from the output signal of a one-dimensional light array sensor.

10. A particle analyzing apparatus according to claim 8, wherein said control means is capable of recognizing the amount of movement of said flow cell.

11. A particle analyzing apparatus according to claim 10, further having means for detecting the amount of movement of said flow cell.

12. A particle analyzing apparatus according to claim 11, wherein said control means is provided with means for stopping said flow cell at the midpoint position of the amount of movement between the two edge portions of said circulation portion.

13. A particle analyzing apparatus according to claim 8, further having means for limiting the range of movement of said flow cell and detecting the arrival of said flow cell at its limit of movement.

14. A particle analyzing apparatus comprising:

an irradiating optical system for applying a light beam to a particle to be examined flowing through a circulation portion in a flow cell;

a photometering optical system for photometering the light from the particle to be examined irradiated by said irradiating optical system;

moving means for rendering a base bed on which said flow cell and said photometering optical system are placed movable relative to said irradiating optical system; and in-focus detecting means for detecting the aligned state of said photometering optical system in the direction of an optic axis thereof with respect to said flow cell.

15. A particle analyzing apparatus according to claim 14, wherein said in-focus detecting means is provided with a focus detecting part for detecting the reflected lights from the front and rear surfaces of said flow cell to the projected light from an in-focus detecting light source projected into said flow cell via an aperture mask having a slit eccentric sidewise from the center of an optical path and effecting in-focus detection, and a signal processing part for adjusting the focus position of said flow cell.

16. A particle analyzing apparatus according to claim 14, wherein said aperture mask is such that the light beam passed through said mask is within the width of the circulation portion of said flow cell.

17. A particle analyzing apparatus according to claim 15, wherein said signal processing part comprises a position detecting part for finding the peak position of the reflected light from the output signal of a position detecting element provided in said focus detecting part, a position data operating part and a comparator for comparing the result of the operation of said operating part with a regular position and thereby putting out a difference signal.

* * * * *

UNITED STATES PATENT AND TRADEMARK OFFICE
CERTIFICATE OF CORRECTION

PATENT NO. : 4,732,479

DATED : March 22, 1988

INVENTOR(S) : Masayuki Tanaka, et al.

It is certified that error appears in the above-identified patent and that said Letters Patent is hereby corrected as shown below:

COLUMN 5
    Line 23, "photom-" should read --photo---;
    Line 24, "etering" should read --metering--; and
    Line 39, "pass" should read --passes--.

COLUMN 6
    Line 13, "1" should read --101--;
    Line 36, "Gassian" should read --Gaussian--;
    Line 37, "saw-tooth-like" should read --sawtooth-like--;
    Line 49, "saw-tooth-like" should read --sawtooth-like--; and
    Line 68, "flow cell 1" should read --flow cell 101--.

COLUMN 7
    Line 5, "flow cell 1" should read --flow cell 101--;
    Line 52, "potentiometer 121" should read --potentiometer 120--;
    Line 54, "a" should read --an--; and
    Line 66, "is flows" should read --flows--.

COLUMN 9
    Line 4, "filter 219" should read --filter 216--

Signed and Sealed this

Eighteenth Day of July, 1989

Attest:

DONALD J. QUIGG

Attesting Officer      Commissioner of Patents and Trademarks